US010398640B2

(12) United States Patent
Widgerow

(10) Patent No.: US 10,398,640 B2
(45) Date of Patent: Sep. 3, 2019

(54) METHODS FOR TREATING SCARS AND AGING SKIN

(71) Applicant: Allergan, Inc., Irvine, CA (US)

(72) Inventor: Alan David Widgerow, Irvine, CA (US)

(*) Notice: Subject to any disclaimer, the term of this patent is extended or adjusted under 35 U.S.C. 154(b) by 0 days.

(21) Appl. No.: 14/935,686

(22) Filed: Nov. 9, 2015

(65) Prior Publication Data
US 2016/0058816 A1 Mar. 3, 2016

Related U.S. Application Data

(63) Continuation of application No. 13/294,957, filed on Nov. 11, 2011, now Pat. No. 9,180,157, which is a continuation of application No. 13/294,116, filed on Nov. 10, 2011, now Pat. No. 8,591,961, which is a continuation-in-part of application No. 12/554,364, filed on Sep. 4, 2009, now Pat. No. 8,071,139.

(60) Provisional application No. 61/094,170, filed on Sep. 4, 2008.

(30) Foreign Application Priority Data

Sep. 18, 2008 (ZA) .................. 2008/08004
Jun. 8, 2009 (ZA) .................. 2009/04000

(51) Int. Cl.
A61K 36/00 (2006.01)
A61K 8/97 (2017.01)
A61K 36/23 (2006.01)
A61K 36/63 (2006.01)
A61K 36/896 (2006.01)
A61K 31/7048 (2006.01)
A61K 36/88 (2006.01)
A61Q 19/00 (2006.01)
A61Q 19/08 (2006.01)
A61K 8/891 (2006.01)
A61K 9/00 (2006.01)
A61K 9/06 (2006.01)
A61K 8/60 (2006.01)

(52) U.S. Cl.
CPC ............... A61K 8/97 (2013.01); A61K 8/602 (2013.01); A61K 8/891 (2013.01); A61K 9/0014 (2013.01); A61K 9/06 (2013.01); A61K 31/7048 (2013.01); A61K 36/00 (2013.01); A61K 36/23 (2013.01); A61K 36/63 (2013.01); A61K 36/88 (2013.01); A61K 36/896 (2013.01); A61Q 19/00 (2013.01); A61Q 19/08 (2013.01); A61K 2800/49 (2013.01); A61K 2800/524 (2013.01); A61K 2800/596 (2013.01); A61K 2800/70 (2013.01); A61K 2800/87 (2013.01)

(58) Field of Classification Search
CPC ...................................................... A61K 36/00
USPC ....................................................... 424/725
See application file for complete search history.

(56) References Cited

U.S. PATENT DOCUMENTS

| 4,707,360 | A | 11/1987 | Brasey |
| 5,368,553 | A | 11/1994 | Newman |
| 5,833,998 | A | 11/1998 | Biedermann et al. |
| 6,159,494 | A * | 12/2000 | Widgerow ........... A61K 9/7023 424/443 |
| 6,261,605 | B1 | 7/2001 | Singh-Verma |
| 6,280,765 | B1 | 8/2001 | Gueret |
| 6,369,116 | B1 | 4/2002 | Wong et al. |
| 6,437,004 | B1 | 8/2002 | Perricone |
| 6,743,449 | B2 | 6/2004 | Pinnell et al. |
| 7,141,252 | B2 | 11/2006 | Soubhie |
| 7,160,560 | B2 | 1/2007 | Pinnell |
| 7,344,737 | B2 | 3/2008 | Pushpangadan et al. |
| 7,402,669 | B2 | 7/2008 | Loiseau et al. |
| 2003/0133969 | A1* | 7/2003 | Bergeron ............. A61K 9/0014 424/449 |
| 2008/0118581 | A1 | 5/2008 | Loiseau et al. |
| 2008/0226700 | A1 | 9/2008 | Cozzolino |
| 2009/0117061 | A1 | 5/2009 | Gross |
| 2010/0303872 | A1 | 12/2010 | Dumas et al. |

FOREIGN PATENT DOCUMENTS

| CA | 1300513 | * | 5/1992 |
| RU | 2121341 | * | 11/1998 |
| WO | 2002-002076 | | 1/2002 |
| WO | 2002-002076 A3 | | 1/2002 |
| ZA | 1997/10846 | | 12/1997 |
| ZA | 2008/02517 | | 3/2008 |
| ZA | 2008/08004 | | 9/2008 |
| ZA | 2009/04000 | | 6/2009 |
| ZA | 2010/05770 | | 8/2010 |

OTHER PUBLICATIONS

Everson, Unexpected Benefits of Olive Leaf Extract, 2013, 49 pages.*

(Continued)

Primary Examiner — Michael V Meller
(74) Attorney, Agent, or Firm — Laura L. Wine

(57) ABSTRACT

Beneficial topical compositions for treating scar or aging skin are provided. In one embodiment, the compositions include *Bulbine frutescens*, *Centella asiatica* and a phenol derived from olives, such as oleuropein. The composition may be used in the treatment of scars formed during surgery. The composition may also be used cosmeceutically in the treatment of aged skin, and may include phosphatidylserine, vitamins, and other beneficial anti-aging ingredients.

3 Claims, No Drawings

(56) References Cited

OTHER PUBLICATIONS

Cho, Soyun, et al., Phosphatidylserine Prevents UV-induced Decrease of Type 1 Procollagen and Increase of MMP-1 in Dermal Fibroblasts and Human Skin in vivio, Journal of Lipid Research, 2009, 1235-1245, 49, American Society for Biochemistry and Molecular Biology, Inc.

Dhar, Arindam, et al., Synthesis, Structure-Activity Relationships, and RARy-Ligand Interactions of Nitrogen Heteroarotinoids, Journal of Med. Chem, 1999, 3602-3614, vol. 42, No. 18, American Chemical Society.

Gelse, K., et al., Collagens-Structure, Function, and Biosynthesis, Advanced Drug Delivery Reviews, 2003, 1531-1546, 55, Elsevier B.V.

Mustoe, Thomas A., et al., International Clinicla Recommendations on Scar Management, Plast Reconstructive Surgery, 2002, 560-571, 110.

Pub Med, 2 pages, 2000, Oleuropein, an antioxidant polyphenol from olive oil, is poorly absorbed from isolated perfused rat intestine. Edgecombe SC1, Stretch GL, Hayball PJ.

Shah, Mamta, et al., Neutralising Antibody to TGF-B1,2 Reduces Cutaneous Scarring in Adult Rodents, Journal of Cell Science, 1994, 1137-1157, 107, The Company of Biologists Limited, GB.

Widgerow, Alan D., Cellular/Extracellular Matrix Cross-Talk in Scar Evolution and Control, Wound Repair and Regeneration, 2011, 117-133, 19, Wound Healing Society.

Widgerow, Alan D., et al., New Innovations in Scar Management, Aesthetic Plastic Surgery, 2000, 227-234, 24, Springer-Verlag New York Inc.

Widgerow, Alan D., Scar Management—The Principles and their Practical Application, WCET Journal, 2011, 18-21, 31.

Widgerow, Alan David, Current Concepts in Scar Evolution and Control, Aesthetic Plastic Surgery, 2011, 628-365, 35, Springer.

Widgerow, Alan David, et al., Scar Management Practice and Science: A Comprehensive Approach to Controlling Scar Tissue and Avoiding Hypertrophic Scarring, Advance Skin Wound Care, 2011, 555-561, vol. 24, Lippincott Williams & Wilkins.

Widgerow, Alan David, Scar Management—Marrying the Practical with the Science, Wound Healing Southern Africa, 2010, 7-10, vol. 3, No. 1.

Wilgus, Traci A., et al., Reduction of Scar Formation in Full-Thickness Wounds with topical Celecoxib Treatment, Wound Repair and Regeneration, 2003, 25-34, 25, Wound Healing Society.

\* cited by examiner

METHODS FOR TREATING SCARS AND AGING SKIN

CROSS-REFERENCE TO RELATED APPLICATIONS

This application is a continuation of U.S. patent application Ser. No. 13/294,957, filed on Nov. 11, 2011, which is a continuation of U.S. patent application Ser. No. 13/294,116, filed Nov. 10, 2011, now U.S. Pat. No. 8,591,961, which is a continuation-in-part of U.S. patent application Ser. No. 12/554,364, filed Sep. 4, 2009, now U.S. Pat. No. 8,071,139, which claims priority from U.S. Patent Application Ser. No. 61/094,170, filed Sep. 4, 2008 and from South African Patent Applications Nos. 2008/08004 and 2009/04000 filed respectively on Sep. 18, 2008 and Jun. 8, 2009, all herein incorporated by reference.

BACKGROUND

Field

Several embodiments of the invention relate to the treatment of skin. In one embodiment, the invention comprises beneficial topical compositions for preventing skin damage and for treating skin that has already been damaged. Damaged skin includes, but is not limited to, photoaged skin, inflamed skin, acne, burns, wounds, age spots, stretch marks, wrinkles, and scars that result from such damage.

Description of Related Art

In U.S. Pat. No. 6,159,494 to Widgerow and Chait, herein incorporated by reference, a method of treating damaged human skin is disclosed. The treatment includes applying to the skin a medicament for topical application (such as an ointment) comprising as the active ingredients *Bulbine frutescens* and, optionally, *Centella asiatica*. The medication is used in conjunction with a tape that is applied to the skin about the scar to, for example, prevent or minimize any tension that is applied to the scar.

SUMMARY

In several embodiments, a composition for effectively treating damaged skin is provided. The skin may have a wound or may exhibit one or more signs of aging. Damaged skin includes, but is not limited to, scars, photoaged skin, inflamed skin, acne, burns, wounds, age spots, stretch marks, wrinkles, dull skin, pores, hyperpigmentation, and hypopigmentation. Thus, in many embodiments, the topical compositions described herein rejuvenate, revitalize and heal the skin.

In one embodiment, the composition comprises a topical composition (e.g., a gel medicament) that comprises, consists essentially of, or consists of at least one extract of *Bulbine frutescens* in an amount from about 0.25% to about 25% mass per mass of the composition, at least one extract of *Centella asiatica* in an amount from about 0.1% to about 25% mass per mass of the composition, and one or more phenols (including, but not limited to compounds extracted from olives and/or olive leaf) in an amount from about 0.1% to about 10% mass per volume of the composition. In one embodiment, the phenol comprises oleuropein. In some embodiments, the composition further comprises one or more of the following: a silicone (e.g., dimethicone), water, a solvent, a preservative, a surfactant, a gelling agent, and a pH balancer. Phosphatidylserine or other phospholipids are included in some embodiments. One or more vitamins are included in several embodiments. In some embodiments, growth factors and/or stem cells are included. In some embodiments, the topical composition comprises at least one extract of *Bulbine frutescens* in an amount from about 1.25 mg to 25 mg, at least one extract of *Centella asiatica* in an amount from about 0.5 mg to 25 mg, and at least one extract of olive (e.g., from the olive fruit or leaf, such as oleuropein) in an amount from about 0.5 mg to 2.5 mg, and optionally dimethicone and/or phosphatidyl serine. In several embodiments, the topical composition comprises one or more *Bulbine*, *Centella*, and glycosides.

In one embodiment, the invention comprises a gel medicament for topical application to damaged skin, said medicament comprising, consisting or consisting essentially of an extract of *bulbine frutescens* in an amount from about 9% to about 11% mass per mass of the medicament, an extract of *Centella asiatica* in an amount from about 0.1% to about 2% mass per mass of the medicament, a phenol (e.g., oleuropein) extracted from a source selected from the group consisting of olive leaf and olive oil in an amount from about 0.18% to about 0.3% mass per volume of the medicament, dimethicone, water, and one or more of the following: propylene glycol, glycerol-polyethylene glycol oxystearate, poloxamer, and phenoxyethanol. Phosphatidylserine is included in some embodiments.

In several embodiments of the invention, a method for treating damaged skin is provided. In one embodiment, the method comprises identifying damaged skin and applying a topical composition to said damaged skin, wherein application of said topical composition treats said damaged skin. The topical composition may comprise any of the various embodiments described herein, and in one embodiment, includes one or more extracts of *Bulbine frutescens*, one or more extracts of *Centella asiatica*, oleuropein (and/or other olive-related compound), and optionally one or more silicones. Anti-aging ingredients may be included in several embodiments.

In several embodiments, the damaged skin is damaged by a wound, a scar, acne, inflammation, stretching of skin (such as with pregnancy, surgery, or weight gain), or aging. In one embodiment, the wound is produced during a surgical procedure. In one embodiment, the application of the composition to the damaged skin reduces inflammation. In one embodiment, the topical application of the composition to the damaged skin unexpectedly produces an occlusive dressing without the use of microporous tape. In one embodiment, the composition facilitates formation of a barrier that protects the damaged skin from environmental influences and provides support for the damaged skin. In several embodiments, the beneficial combination of *Bulbine*, *Centella* and oleuropein (and/or other olive-related compound) works synergistically, and has several advantages over a combination of *Bulbine* and *Centella* alone.

In several embodiments, the invention comprises a topical composition for the treatment of damaged skin, comprising one or more extracts of *Bulbine frutescens*, one or more extracts of *Centella asiatica*, one or more olive extracts, and, optionally, one or more silicones. The olive extract comprises oleuropein in one embodiment. The silicone may comprise dimethicone. In one embodiment, extracts of *Bulbine frutescens* are provided in a range of about 0.25% to about 25% mass per mass of the topical composition, extracts of *Centella asiatica* are provided in a range of about 0.1% to about 10% mass per mass of the topical composition, and olive extracts are provided in a range of about 0.1% to about 5% mass per volume of the topical composition.

In several embodiments, the topical composition is in the form of a gel, cream or ointment. In one embodiment, the topical composition further comprises at least one ingredient selected from the group consisting of water, a solvent, a preservative, a surfactant, a gelling agent, and a pH balancer. In one embodiment, all of these ingredients are combined with *Bulbine, Centella*, and olive extracts.

In some embodiments, the topical composition further comprises at least one ingredient selected from the group consisting of phospholipids, amino acids, vitamins and peptides. In one embodiment, the topical composition includes phosphatidylserine.

In several embodiments, the topical composition is used to treat damaged skin. Damaged skin includes, but is not limited to, wounded skin, scarred skin, and aging skin. Damaged skin may have age spots, stretch marks, wrinkles, or combinations thereof. Damaged skin may exhibit laxity.

In some embodiments, the topical compositions described herein are used without the use of microporous tape or other support structure. In one embodiment, the topical compositions are sufficiently viscous or sticky to produce an occlusive dressing without a support structure. In several embodiments, a topical composition is applied beneath a support structure (e.g., tape). In other embodiments, a topical composition is applied on top of a support structure (e.g., tape). In one embodiment, the tape is a microporous tape that is designed to accept the topical composition on the outer surface of the tape and deliver the topical composition in contact with the damaged skin through, for examples, pores or other conduits. In yet other embodiments, a user is instructed to apply a topical composition both below and on top of a support structure (e.g., tape).

In several embodiments, the topical compositions are provided in a delivery device (such as a multi-chambered device) that separates one or more ingredients from other ingredients. For example, the *Bulbine, Centella*, olive extracts and/or silicone may be separated from one or more additional ingredients in a dual-chambered device. The topical compositions may be applied daily or on an as needed basis. Individual ingredients may be applied either simultaneously or sequentially.

DETAILED DESCRIPTION

Several embodiments of the invention comprise an effective composition for preventing skin damage and for treating skin that has already been damaged. Damaged skin includes scars, photoaged skin, inflamed skin, acne, burns, wounds, age spots, stretch marks, wrinkles, dull skin, pores, hyperpigmentation, and hypopigmentation. In several embodiments, the topical composition comprises one or more extracts of *Bulbine frutescens, Centella asiatica*, olive extract (e.g., olive oil, olive leaf extract) and, optionally, one or more silicones. Anti-aging ingredients, such other plant extracts, phospholipids, vitamins, minerals, peptides, amino acids, growth factors, essential oils, and stem cells are further included in several embodiments.

*Bulbine*

In several embodiments, the invention comprises one or more extracts of *Bulbine*. Extracts may be obtained from any part of the plant, including the leaves, stems, flowers, fruits, bark, and roots. *Bulbine frutescens* is a common garden plant that is native to South Africa. In several embodiments of the invention, the use of *Bulbine frutescens* is particularly advantageous because of its hydrating properties. In several embodiments, one or more glycoproteins from *Bulbine frutescens* are sufficiently large to remain on the surface of the skin long enough to produce effective hydration of the skin. Additionally, in some embodiments, the extracts (e.g., peptides or other compounds) of *Bulbine frutescens* have decorin-like effects on wound healing, and improve mature collagen deposition in healing wounds. In some embodiments, compositions comprising *Bulbine* are especially effective because one or more polypeptides mimic the effect of decorin and rearrange collagen in a uniform manner during the process of fibrillogenesis and collagen regeneration. In some embodiments, the use of *Bulbine, Centella*, and olive extracts (e.g., *Bulbine frutescens, Centella asiatica*, and oleuropein) is effective in modulating, uniformly arranging, and maturing collagen during the process of healing. Thus, in some embodiments, the topical composition not only stimulates new collagen formation, but packages the new fibres in a uniform and structured manner. In one embodiment, the topical compositions disclosed herein contain agents that affect decorin activity or mimic decorin to facilitate collagen remodeling and structural arrangement.

*Centella*

*Centella asiatica* is a small herbaceous annual plant. Extracts, such as asiaticosides, asiatic acid and triterpenes, may be obtained from any part of the plant, including the leaves, stems, flowers, fruits, bark, and roots. In several embodiments, the invention comprises one or more extracts of *Centella asiatica*, or other *Centella* species. In one embodiment, *Centella asiatica* is used to decrease inflammation, stimulate type 1 collagen production, and/or act as anti-oxidant.

In one embodiment, compositions comprising *Centella* are used in scar management. In some cases, the more quickly a scar matures the less chance there is of hypertrophy. Collagen maturation goes through phases with collagen type III being present in greater levels in the early scarring phase. As the scar matures the ratio of type III to type I returns to normal levels. Thus, in several embodiments, the invention comprises one or more ingredients that encourages type I collagen formation. In some embodiments, one or more extracts of *Centella asiatica* increase levels of mature collagen and facilitate normalization of collagen ratios. In several embodiments, purified extracts (triterpenic fractions, including asiaticoside and other saponins) of the *Centella* plant are used.

TGFβ is the prototype of a protein superfamily that has been recognised as a fibroproliferative and collagen stimulating agent involved in excess scarring (particularly TGF-β1). Many isoforms of the protein exist with most isoforms sharing the same fibroproliferative properties. One isoform, TGF-β3 however, appears to have a protective effect against excess collagen formation counteracting the TGF-β1 effects. According to one embodiment, asiaticoside can down-regulate TGF-β1 mRNA and TIMP1 expressions and upregulate TGF-β3 mRNA expression in post burn hypertrophic scars, and is also capable of decomposing the products of type I collagen, contributing to the reduction of hypertrophic scar formation. Thus, in several embodiments, the invention comprises one or more agents (such as asiaticoside) to modulate TGFβ activity.

Olive Extracts

In several embodiments, the invention comprises one or more extracts of olive (e.g., olive oil, olive leaf extract, etc.). Extracts include, in several embodiments, phenolic compounds. Extracts, which may or may not be in the form of oil (or derived from an oil), may be obtained from any part of the olive tree including the leaves, stems, flowers, fruits, bark, and roots. In one embodiment, the invention comprises, consists essentially of or consists of *Bulbine, Centella* and an olive extract (e.g., oleuropein). In one embodiment, oleuropein and other agents may be extracted from the leaves of the olive tree. In some embodiments, engineered or synthesized phenols may be used in the compositions described herein. In some embodiments, oleuropein and/or additional constituents provide for a multimodality approach to scar management covering all phases of the wound healing cascade. For example, for certain scar applications, an important physiologic response to wounding is that of inflammation. Inflammation can also be one of the most destructive: over exuberant inflammation is thought to be cause of most chronic arthritic conditions, heart disease, and chronic wound pathogenesis. Along the physiologic path to scar formation, excess inflammation will result in an exaggerated scar. Suture materials are frequently associated with this phenomenon. On the other hand, controlled inflammation may speed up the process of scar maturation with minimal fibrosis. Thus, in several embodiments, the invention provides a therapeutic balance by facilitating controlled inflammation (e.g., by achieving a balance between no inflammation and excess inflammation). Thus, surprisingly, in several embodiments, the compositions disclosed herein maintain a certain amount of inflammation to ensure optimal healing.

Phenols (e.g., oleuropein, oleocanthal) extracted from olives have known anti-inflammatory and antibacterial properties. In several embodiments, the invention comprises low doses of one or more phenols (whether extracted from the olive plant or not) in combination with *Bulbine frutescens* and *Centella asiatica* such that helpful inflammation is unaffected, whereas exuberant inflammation, typical of foreign body reactions, is down-regulated or modulated. In some embodiments, the invention comprises one or more *Bulbine, Centella*, and glycosides (including, but not limited to, oleuropein).

In several embodiments of the invention, the topical compositions described herein include one or more extracts of olive, which are used to achieve controlled inflammation. It is well-accepted that ongoing inflammation retards wound healing. This is especially important in chronic non-healing wounds where proteases and reactive oxygen metabolites are responsible for much on the ongoing damage, antiproliferative effects, and non-healing seen in these wounds. The negative effects of exuberant inflammation are not limited to chronic wounds: in acute wounds low-grade ongoing inflammation results in increased matrixmetalloproteinase and cytokine elaboration (especially TGF-β1 and 2, Il-1,6,8) and a profibrotic state with a resultant exaggerated scar. This inflammation can be initiated by tension on the scar, foreign material (long-standing subcuticular sutures), bacteria, biofilm, and many other scenarios. Thus, control of inflammation during the healing phase is a desired goal of several embodiments of the invention. In several embodiments of the invention, at least one olive extract is provided. Olive extracts, such as olive oil (e.g., newly pressed extra-virgin olive oil) and extracts of olive leaf, contain phenolic compounds (oleocanthal, oleuropein) that act as a natural anti-inflammatory compound that has a potency and profile strikingly similar to that of ibuprofen, without the undesired side effects. Although structurally dissimilar, both these molecules inhibit the same cyclo-oxygenase enzymes in the prostaglandin-biosynthesis pathway. According to several embodiments, this anti-inflammatory effect has important implications for scar control. Thus, in several embodiments, the topical composition inhibits cyclo-oxygenase enzymes. In several embodiments, olive extracts include one or more of the following: hydroxytyrosol, oleocanthal, oleuropein, rutin, apigenin, and luteolin.

In several embodiments, olive extracts are used to stimulate proteasome function and promote normal fibroblast (reverses senescence) activity with formation of new collagen. Proteasomes "mop up" fragmented protein particles including fragmented collagen, thereby minimizing the formation of undesired clumped collagen.

Silicone

In several embodiments, the invention comprises one or more silicones. In some embodiments, the invention comprises, consists essentially of, or consists of one or more extracts of *Bulbine, Centella*, phenols or an olive extract, and silicone. Silicones include, but are not limited to dimethicone and cyclomethicones. In one embodiment, the silicone is either in the form of sheeting or a gel. In one embodiment, the silicone, when used in conjunction with *Bulbine frutescens* and *Centella asiatica*, provides a synergistic complement to the action of *Bulbine frutescens* as a hydrating agent. In one embodiment, dimethicone is added to the mix as an extremely efficient hydrating agent complementing the action of *Bulbine frutescens*. In some embodiments, the addition of an olive extract with silicone results in a beneficial sticky barrier.

Normal skin has a mature stratum corneum characterised by minimal transepidermal water loss. Dehydration of the stratum corneum initiates signaling to keratinocytes. These keratinocytes are stimulated to produce cytokines which activate dermal fibroblasts to synthesize and release collagen. Excessive collagen production may lead to abnormal scarring. In one embodiment of the invention, silicone is provided as an effective barrier to water loss and stratum corneum breach. Silicone may be provided in the form of sheeting, gels (e.g., dimethicone), or other appropriate forms.

Phosphatidylserine

In several embodiments, the topical compositions comprise phosphatidylserine. In the context of collagen modulation, particularly when considering anti-aging intervention, the *Bulbine, Centella*, an olive extract (e.g., oleuropein), and optionally silicone, may be used in conjunction with phosphatidylserine. In one embodiment, phosphatidylserine stimulates the formation of procollagen, a collagen precursor. This new collagen is then acted on by the combination of *Bulbine, Centella*, and olive extract(s), and/or other optional ingredients, to induce maturation of the collagen. In one embodiment, this sequence has important synergistic anti-aging benefits in several embodiments. In one embodiment, phosphatidylserine also decreases matrixmetalloproteinase 1 (MMP1) levels which promotes collagen and extracellular matrix breakdown characteristic of photodamaged skin. It then stimulates the formation of new collagen by promoting procollagen formation.

Examples of Additional Ingredients & Ranges

In several embodiments, the topical compositions comprise one or more additional ingredients. These additional ingredients, along with *Bulbine, Centella*, olive extracts, silicone, and phosphatidylserine, are provided in a range of about 0.1% to about 50%, or higher, according to several embodiments (e.g., 0.1%-1%, 1%-2%, 2%-5%, 5%-10%, 10%-25%, 25%-50%, and overlapping ranges thereof). As with other percentages disclosed herein, these percentages may be mass per mass, mass to volume, or volume to volume with respect to the total composition. In some embodiments, the ingredients of the topical compositions disclosed herein are provided in amounts ranging from about 1 μg to about 1 g, or higher (e.g., 1 μg-2 μg, 2 μg-5 μg, 5 μg-10 μg, 10 μg-25 μg, 25 μg-100 μg, 100 μg-500 μg, 500 μg-1 mg, 1 mg-5 mg, 5 mg-10 mg, 10 mg-20 mg, 20 mg-30 mg, 30 mg-40 mg, 40 mg-50 mg, 50 mg-60 mg, 60 mg-70 mg, 70 mg-80 mg, 80 mg-90 mg, 90 mg-100 mg, 100 mg-250 mg, 250 mg-500 mg, 500 mg-1 g, or higher, and overlapping ranges thereof). These amounts may be the weight of the ingredient per individual application (or dose), per unit or per container (tube, bottle, jar, etc.). Individual applications may be made hourly, 1-10 times per day, weekly, or as needed.

For example, in some embodiments, one or more of the following ingredients are included, along with extracts of *Bulbine, Centella*, olive, and optionally silicone and/or phosphatidylserine: other plant extracts and vitamins or provitamins for the purpose of formulating a comprehensive cosmetic skin maintenance range achieving cleansing, moisturizing, healing, toning, hydrating, and protecting the skin. These extracts, vitamins and provitamins include, but are not limited to: *Symphytum officinale*, provitamin B5, *Hamamelis virginiana, Cucumis sativus*, zinc, *Enantia chlorantha*, German camomile (bisabolol), retinyl palmitate, *Macrocystis pyrifera*, prolamins, and *Imperata cylindrical*, white tea-leaf extract, Calcium α-hydroxymethionine, homotaurine, matrikines, hydrosolanum, and hesperidum.

In some embodiments, the composition includes one or more plant extracts (such as *Bulbine*) combined with one or more of the following: one or more *Centella* extracts, one or more olive extracts, phospholipids (e.g., phosphatidylserine), vitamins (e.g., vitamin A, B, C, and/or D), minerals (e.g., calcium, magnesium, and copper), acids (e.g., hyaluronic acid, salicylic acid, (mandelic acid, and fruit acids), cells or cellular extracts, fats or oils (e.g., shea butter, argan oil, and coconut oil), fruit extracts (e.g., citrus, acai, goji, blueberry, and acerola), caffeine, green tea extracts, essential oils, enzymes, and coenzymes (e.g., ubiquinone).

The active compounds described herein may be formulated for administration in a pharmaceutical carrier in accordance with known techniques. See, e.g., Remington, The Science And Practice of Pharmacy (9$^{th}$ Ed. 1995), herein incorporated by reference. In the manufacture of a composition according to several embodiments of the invention, the active compound (including the physiologically acceptable salts thereof) may be admixed with, inter alia, an acceptable carrier. The carrier is acceptable in the sense of being compatible with any other ingredients in the composition and must not be deleterious to the patient. The carrier may be a solid or a liquid, or both, and may be formulated with the compound as a unit-dose formulation, for example, a tablet, which may contain from 0.01% or 0.5% to 95% or 99% by weight of the active compound. One or more active compounds may be incorporated in the compositions of the invention, which may be prepared by any of the well-known techniques of pharmacy comprising admixing the components, optionally including one or more accessory ingredients. Carriers which may be used include petroleum jelly, lanoline, polyethylene glycols, alcohols, transdermal enhancers, and combinations of two or more thereof. In some embodiments, the topical composition is partially or fully incorporated in delivery vehicles such as microspheres or nanoparticles, or are encapsulated (e.g., in liposomes). In some embodiments, a topical composition is pre-impregnated in/on a support structure (e.g., tape, patch, bandage, etc.).

In addition to one or more active compounds, the topical compositions disclosed herein comprise other additives, such as pH-adjusting additives. In some embodiments, useful pH-adjusting agents include acids, such as citric acid or lactic acid, bases or buffers, such as sodium lactate, sodium acetate, sodium phosphate, sodium citrate, sodium borate, or sodium gluconate.

The compositions may contain antimicrobial preservatives in some embodiments. In several embodiments, antimicrobial preservatives include, but are not limited to, methylparaben, propylparaben, benzyl alcohol, ethylhexylglycerin, potassium sorbate, phenoxyethanol, EDTA, grapefruit seed extract, tea tree oil, sodium benzoate, dehydroacetic acid, and combinations thereof. In some embodiments, anti-fungal preservatives are used alone or in combination with anti-bacterial preservatives. In one embodiment, the topical compositions are paraben-free. In one embodiment, an antimicrobial preservative is used when the formulation is placed in a vial designed for multi-dose use. In some embodiments, the compositions disclosed herein comprise anti-biofilm anti-microbial agents such as lactoferrin, xylitol, farnesol gallium, dispersin B, EDTA, and furanone compounds, or combinations thereof. In one embodiment, the composition comprises *Bulbine, Centella*, olive extract (e.g., oleuropein) and one or more anti-biofilm agents. The compositions according to some embodiments may be lyophilized using techniques well known in the art.

In several embodiments, the topical compositions disclosed herein comprise agents that stimulate production of extracellular matrix components. These agents include, but are not limited to, matrikines, peptides and their lipophilic derivatives, plant extracts, and polyols. Specific ingredients include one or combinations of the following as examples: *Centella asiatica*, niacinamide, tetrahexyldecyl ascorbate, palmitoyl tetrapeptide-5, palmitoyl oligopeptide, palmitoyl tetrapeptide-7, palmitoyl dipeptide-5, diaminobutyroyl hydroxythreonine, siegesbeckia orientalis, rabdosia rubescens, rice extract, olive oil, jojoba oil, pichia pastoris, resveratrol, tripeptide-10 citrulline, acetyl dipeptide-1 cetyl ester, and phosphatidylserine, and extracts or salts/acids thereof. One or more of these ingredients are combined with a *Bulbine* extract in several embodiments.

In several embodiments, the topical compositions disclosed herein comprise agents that decrease the degradation of extracellular matrix components. The agents include, but are not limited to, plant extracts, vitamins, and peptides. Specific ingredients include one or combinations of the following as examples: blackberry leaf, *Centella asiatica*, tetrahexyldecyl ascorbate, siegesbeckia orientalis, rabdosia rubescens, actinidia chinensis, sophora angustifolia, dipalmitoyl hydroxyproline, glycine soya protein, and phosphatidylserine, and extracts or salts/acids thereof. One or more of these ingredients are combined with a *Bulbine* extract and/or an olive extract in several embodiments.

In several embodiments, the topical compositions disclosed herein comprise agents that improve fibroblast adhesion to extracellular matrix, including, but not limited to, yeast extract, peptides, and plant extracts. Specific ingredients include one or combinations of the following as examples: pichia pastoris, hexapeptide-10, and *Bulbine*, and extracts or salts/acids thereof. One or more of these ingredients are combined with a *Centella* extract and/or an olive extract in several embodiments.

In several embodiments, the topical compositions disclosed herein comprise agents that alter melanin production and distribution, including, but not limited to, vitamins, plant extracts, aldehydes, glycosides, and peptides. Specific ingredients include one or combinations of the following as examples: niacinamide, tetrahexyldecyl ascorbate, alpha arbutin, siegesbeckia orientalis, rabdosia rubescens, actinidia chinensis, sophora angustifolia, pomegranate, and extracts or salts/acids thereof. One or more of these ingredients are combined with a *Bulbine* extract, *Centella* extract and/or an olive extract in several embodiments.

In several embodiments, the topical compositions disclosed herein comprise agents that improve barrier structure and function, including, but not limited to, polyols, ceramides, sterols, plant extracts, peptides. Specific ingredients include one or combinations of the following as examples: xylitylglucoside, anhydroxylitol, xylitol, ceramide 2, ceramide 3, hydroxypropyl bispalmitamide MEA, glycine soya sterols, niacinamide, *Bulbine*, and extracts or salts/acids thereof. One or more of these ingredients are combined with a *Centella* extract and/or an olive extract in several embodiments.

In several embodiments, the topical compositions disclosed herein comprise agents that reduce glycation, including, but not limited to, plant extracts, vitamins, peptides. Specific ingredients include one or combinations of the following as examples: *Centella Asiatica*, vitamin B-6, and L-carnosine, and extracts or salts/acids thereof. One or more of these ingredients are combined with a *Bulbine* extract and/or an olive extract in several embodiments.

In several embodiments, the topical compositions disclosed herein comprise agents that improve skin hydration, including, but not limited to, amino acids, polyols, plant extracts, vitamins, and saccharides. Specific ingredients include one or combinations of the following as examples: *Bulbine*, xylitylglucoside, anhydroxylitol, xylitol, betaine, and niacinamide, and extracts or salts/acids thereof. One or more of these ingredients are combined with a *Centella* extract and/or an olive extract in several embodiments.

In several embodiments, the topical compositions disclosed herein comprise antioxidants. In one embodiment, antioxidants are useful for modulating appropriate collagen crosslinking. Linkages need to be susceptible to MMP breakdown to ensure balanced degradation and neosynthesis. Pyridinoline crosslinks, not normally seen in skin, may be undesired because they are able to withstand major force and tend to be resistant to MMP-1 degradation. This pyridinoline phenomenon has been linked to oxygen radical activity (especially in burns); thus, antioxidants appear to be beneficial in potential scar reduction according to several embodiments. Antioxidants useful in several embodiments include, but are not limited to, superoxide dismutase, catalase, glutathione peroxidase, glutathione, ascorbic acid, and tocopherol. In several embodiments, extracts of *Centella asiatica* and olive (e.g., oleuropein) are used as antioxidants.

In several embodiments, the topical compositions disclosed herein comprise anti-bruising agents. Such agents include, but are not limited to, arnica. Agents or devices that modulate the temperature of the target tissue are provided in some embodiments, and may also help with bruising.

In several embodiments, the topical compositions disclosed herein comprise agents or devices that modulate extracellular shear force pressure on the inside of the wound. In one embodiment, by decreasing hydrostatic, osmotic, and therefore internal fluid shear forces, less tension is generated on the wound intrinsically. Thus, in some embodiments, hygroscopic agents are included in the compositions disclosed herein. Hygroscopic agents include, but are not limited to, honey, carboxymethylcellulose, glycerol, sugar, aloe vera powder, and other ingredients that, for example, sequester or absorb fluid from the damaged tissue.

In one embodiment, the composition comprises a topical composition (e.g., a gel medicament) that comprises, consists essentially of, or consists of an extract of *Bulbine frutescens* in an amount from about 0.25%-25% (e.g., 5%, 9% or 9.9% to about 11%) mass per mass of the composition; an extract of *Centella asiatica* in an amount from about 0.01%-10% (e.g., 0.1%-2%) mass per mass of the composition; a phenol (e.g., extracted from the olive fruit, leaf, etc.) in an amount from about 0.01%-5% (e.g., 0.18%-0.3%) mass per volume of the composition. In some embodiments, the phenols comprise about 0.18% to 0.3% mass/volume of the medicament when used for the treatment of damaged skin such as skin cut in an operation and about 0.018% to 0.03% when the composition is used for cosmetic purposes. In one embodiment, the *Centella asiatica* may comprise from about 0.45% to 0.55% (e.g., about 0.5%) mass per mass of the composition.

In several embodiments, the invention comprises, consists essentially of, or consists of a topical composition comprising one or more extracts of *Bulbine*, one or more extracts of *Centella*, phenols or one or more olive extracts, and silicone. In one embodiment, the topical composition comprises, consists essentially of, or consists of *Bulbine frutescens* extract, *Centella asiatica* extract, oleuropein, and dimethicone. In several embodiments, the ingredients are provided in the following amounts: one or more extracts of *Bulbine* at about 0.25% to 75%, one or more extracts of *Centella* at about 0.11% to 50%, phenols or one or more olive extracts at about 0.1% to 40%, and silicone at about 0.1% to 20%. Percentages can be mass/mass, volume/volume, or mass/volume.

In several embodiments, the topical composition may comprise, consist essentially of, or consist of two or more of the following: (i) *Bulbine* (e.g., *Bulbine frutescens* extract), (ii) *Centella* (e.g., *Centella asiatica* extract), (iii) at least one olive extract (e.g., oleuropein or other phenol), (iv) at least one silicone, and (iv) at least one a pharmaceutically acceptable carrier, wherein the ingredients are provided in an amount from about 0.0001, 0.001, 0.01, or 0.1% by weight to about 1, 2, 5 or 10% by weight, or up to 90, 95 or 99% by weight (e.g., in some embodiments, at least about 0.1%, 1%, 5%, 10%, or 15%).

In several embodiments, the topical composition may comprise, consist essentially of, or consist of two or more of the following: (i) at least one *Bulbine frutescens* extract (ii) at least one *Centella asiatica* extract, (iii) at least one extract from olive oil or olive leaf, (iv) at least one silicone, (v) at least one gelling agent, (vi) at least one pH-balancing agent, (vii) at least one solvent, and (viii) at least one preservative, wherein the ingredients are provided in an amount from about 0.001% by weight to about 95% percent by weight (e.g., 0.1%-5%, 5%-10%, 10%-15%, 15-20%, 20%-25%, 25%-50%, or 50%-75%, or overlapping ranges thereof). The non-active ingredients may be varied as desired as may the proportions of such ingredients. The proportions of the active ingredients may be also be varied. For example, in one embodiment, the amount of *Centella asiatica* is provided in the range of between about 0.1% and 0.25% to produce a milder medicament where the goal is texture modification, e.g. when treating skin that is damaged as a result of aging or damage by excessive exposure to ultra violet light, or when preventing damage. In one embodiment, the oleuropein content will be reduced by a factor of ten (to e.g., 0.018 to 0.03% mass to volume of the final preparation of the topical composition) for use as a cosmetic. In many embodiments, higher concentrations of *Centella* extracts are used, even for preventative or daily cosmetic uses.

In several embodiments, the topical composition may comprise, consist essentially of, or consist of two or more of the following ingredients: 0.10-5.0% *Centella Asiatica* extract, 0.25-5.0% *Bulbine Frutescens* extract, 0.10-0.50% of a phenol extracted from an olive extract (e.g., oleuropein), and 0.10-5.0% phosphatidylserine. In alternative embodiments, the topical composition may also comprise, consist essentially of, or consist of one or more of the following ingredients listed on Table 1 in addition to, or instead of, the ingredients listed above:

TABLE 1

Pyridoxine Tris-Hexyldecanoate - 0.25-5.0%
Tetrahexyldecyl Ascorbate - 0.25-5.0%
Niacinamide - 0.50%-5.0%
Hexapeptide-10 - 0.0001-1.0% (pure peptide basis)
Acetyl Dipeptide-1 Cetyl Ester - 0.0001-1.0% (pure peptide basis)
Tocotrienol - 0.05-3.0%
Dipalmitoyl Hydroxyproline - 0.20-5.0%
Palmitoyl Tripeptide-5 - 0.0001-1.0% (pure peptide basis)
Pamitoyl Oligopeptide - 0.0001-1.0% (pure peptide basis)
Palmitoyl Tetrapeptide-7 - 0.0001-1.0% (pure peptide basis)
Palmitoyl Dipeptide-5 Diaminobutyroyl Hydroxythreonine - 0.0001-1.0% (pure peptide basis)
Palmitoyl Dipeptide-5 Diaminohydroxybutyrate - 0.0001-1.0% (pure peptide basis)
*Siegesbeckia Orientalis* Extract - 0.25-5.0%
*Rabdosia Rubescens* Extract - 0.25-5.0%
*Actinidia Chinensis* (Kiwi) Fruit Water v 0.25-5.0%
*Sophora Angustifolia* Root Extract - 0.25-5.0%
*Helianthus Annuus* (Sunflower) Seed Oil - 0.25-5.0%
*Lupinus Albus* Seed Extract - 0.25-5.0%
*Glycine Soja* (Soybean) Protein - 0.25-5.0%
*Oryza Sativa* (Rice) Extract - 0.25-5.0%
*Artemia* Extract - 0.25-5.0%
Hydrolyzed Rice Extract - 0.25-5.0%
*Simmondsia Chinensis* (Jojoba) Seed Extract - 0.25-5.0%
Blackberry Leaf Extract - 0.25-5.0%
*Pichia pastoris* Ferment Extract - 1.0-25%
*Pichia pastoris*/Resveratrol Ferment Extract - 0.50-5.0%
Xylitylglucoside - 0.10-5.0%
Anhydroxylitol - 0.10-5.0%
Xylitol - 0.10-5.0%
L-Carnosine - 0.10-5.0%

In further embodiments, the composition comprises some or all of the following ingredients: aqua; *bulbine frutescens*, caprylic/capric triglyceride, glycerin, stearic acid, d-panthenol, cetearyl alcohol, lanolin oil, phosphatidylserine, cetyl phosphate; tocopheryl acetate; cetearyl ethylhexanoate, isopropyl myristate, sodium polyacrylate, mineral oil, trideceth-6, triterpenic glycosides of *Centella asiatica*, alpha bisabolol; phenoxyethanol, potassium hydroxide, xanthan gum, oleuropein, methylhydroxybenzoate, butylated hydroxy toluene; fragrance, and retinyl palmitate. In yet further embodiments, the topical composition may also comprise, consist essentially of, or consist of one or more of the following ingredients listed on Table 2 in addition to, or instead of, the ingredients listed above:

TABLE 2

Water - q.s., which in on embodiment acts as a solvent
Arachidyl Alcohol - 0.10-5.0%, which in one embodiment acts as an Emulsifier
Behenyl Alcohol - 0.10-5.0%, which in one embodiment acts as an Emulsifier
Arachidyl Glucoside - 0.10-5.0%, which in one embodiment acts as an emulsifier
Dimethicone - 0.25-3.0%, which in one embodiment acts as an emollient
Olive Extract (e.g., oil) - 0.25-5.0%, which in one embodiment acts as an emollient
Phenoxyethanol - 0.50-1.25%, which in one embodiment acts as a preservative TABLE 2-continued Disodium EDTA - 0.02-0.30%, which in one embodiment acts as a chelating Agent
Carbomer - 0.05-1.0%, which in one embodiment acts as a thickening Agent
Polyacrylate-13 - 0.10-5.0%, which in one embodiment acts as a thickener and/or stabilizer
Polyisobutene - 0.10-5.0%, which in one embodiment acts as an emollient and/or a stabilizer
Polysorbate 20 - 0.10-5.0%, which in one embodiment acts as an emulsifier
Potassium Sorbate - 0.05-1.0%, which in one embodiment acts as a preservative
Ethylhexylglycerin - 0.05-1.0%, which in one embodiment acts as a preservative Standard extraction processes can be used to manufacture the olive, *Bulbine* extract and *Centella* extracts. Maceration, cold-pressing, solvent extraction, and distillation, or combinations therefore, are used in some embodiments. In one embodiment, extracts of olive leaf are produced by extracting in ethanol, drying, and sifting through, for example, a 25 mesh screen. In one embodiment, *bulbine* leaves are expressed and filtered to produce an extract. In one embodiment, *Centella* is extracted in water and alcohol and sifted through, for example, an 80 mesh screen. In some embodiments, further isolation and purification steps are used.

Examples of Forms, Tapes and Support Structures

Several embodiments of the topical compositions described herein can be in the form of an ointment, cream, lotion, paste, gel, spray, aerosol, powder, oil, or combinations thereof. In some embodiments, the invention comprises a device that compartmentalizes the ingredients until time of application. For example, in one embodiment, one or more ingredients are separated from other ingredients until a user combines them. In some embodiments, a dual chamber or multi-chamber device is used to hold and/or apply the topical composition.

In one embodiment, the invention comprises a kit that includes extracts of *Centella asiatica*, *Bulbine frutescens*, olive, and silicone. In other embodiments, the compositions described herein can be provided on a patch for e.g., controlled time release. In yet other embodiments, the compositions described herein can be formulated into capsules, tinctures or other forms for oral consumption (e.g., compositions comprising extracts of *Bulbine*, *Centella*, olive, and/or phosphatidylserine, and optionally other plant extracts and vitamins), and may be particularly well-suited in a nutraceutical regime that is combined with a topical skin care plan.

In one embodiment, a topical application to minimize scarring comprising support, hydration, collagen maturation and controlled inflammation is provided. In one embodiment, a tape or other support structure (e.g., bandage, patch. etc.) is applied to a wound or scar. Supporting a scar, particularly a long scar, in areas where vector forces continually pull on the scar, is provided in some embodiments. For example, in the presternal chest area, forces may be generated on the scar from neck movements, shoulder movements, arm movements and additionally from the weight of breasts in some women. The direct response to such vector forces is increased production of collagen in an effort to keep the wound closed. Thus, in some embodiments, a tape may be particularly helpful in scar treatment. In some embodiments, using agents such as Vitamin E (especially when used early) can cause major skin sensitivities and have a collagenase-like effect, which weakens the scar and can have adverse consequences with stretching and even opening of the scars. Thus in embodiment of the invention, the composition does not include Vitamin E and/or any agent having collagenase-like activity.

In one embodiment, a scar support comprising a microporous tape is provided. In one embodiment, the tape is applied longitudinally along the scar path and not at right angles to facilitate consistent support. In one embodiment, the tape is left in place for days until it spontaneously separates. Premature removal may result in skin stripping which sets up inflammation with negative consequences on the scar. Although small areas of scars may not need support, some small scars do very well with support. For example, cuts on fingers are continually stressed with forces, and thus applying a single layer of microporous tape supports the scar, avoids maceration as seen with common plasters, and allows the application of additional agents to the tape surface to speed up the maturation process. In one embodiment, the tape comprises thin layers that can be applied over one another, thereby obviating the need to remove the tape. In one embodiment, one or more layers are dissolvable. Support structures (such as tape), according to several embodiments, comprise polyethylene, hydrogel, silicones, cotton, silk, polyester, fabric, foam, plastic, elastic, various adhesives, collagen, etc. and combinations thereof.

In one embodiment, a tape (or other support structure) is applied to the length of the scar and the topical composition is applied to the tape. The application of the tape and gel may be commenced as soon as convenient after the wound has been formed. In one embodiment, the tape is a microporous tape that permits contact of the topical composition with the skin when the topical composition is applied over the tape. In some embodiments, the topical composition is applied to the skin before the tape is placed. In that situation, the tape may be porous or not. In some embodiments, the topical composition comprising extracts of *Bulbine, Centella*, olive, and silicone achieves a short-term sticky consistency that works synergistically with the tape. In one embodiment, the tape saturated with the topical composition (e.g., gel) adheres to the wound more effectively than previous formulations.

In one embodiment, a user is instructed to use a tape (or other support structure) and keep the tape in place during bathing. The tape need only be replaced once spontaneous separation takes place (e.g., 3-5 days). Gel may be applied to the surface of the tape twice a day and the routine is continued until scar maturation (e.g., white color) takes place. In one embodiment, the tape component may be stopped anywhere from six weeks of application if the scar is seen to be maturing well, and gel is then applied directly to the scar. In one embodiment, the topical compositions described herein is effective within 6 weeks of using the tape, as compared to longer periods (e.g., 6 months) of using the tape with other compositions. In one embodiment, the topical composition (e.g., gel) is used under the support structure (e.g., tape). For example, gel may be applied as a "worm-like" application to the surface of a scar or wound, not massaged, and covered completely by the tape which overlaps non-affected skin on all sides ensuring adhesiveness. The user may bathe with tape and gel in place, and after approximately three days, the tape may be removed (e.g., while bathing). Subsequently, the scar or wound is washed and the gel re-applied and then covered with new tape. The user is instructed to continue this treatment until the color of damaged skin whitens.

In a further embodiment, the topical composition (e.g., gel) may be applied as a narrow thin film-like application directly and limited to the scar surface keeping surrounding areas free from gel ensuring good adhesion of tape to the gel applied scar surface. This routine is repeated at every dressing/tape change. The user may bathe with tape and gel in place, and after approximately three days, the tape may be removed (e.g., while bathing). Subsequently, the scar or wound is washed and the gel re-applied and then covered with new tape. After 4-6 weeks, according to one embodiment, the tape application may be discontinued and the user is instructed to use the gel directly on the scar surface twice a day until scar maturation is observed by flattening and color change (pink to white color in white skin, dark black/brown to light/very light brown in darker skin).

In a further embodiment, the topical composition (e.g., gel) may be applied directly to the scar surface twice a day after 2, 3, or 4 weeks of supportive tape therapy.

In several embodiments, a tape or other support structure is not needed to treat a scar because the consistency of the topical composition provides sufficient support. For example, in one embodiment, the topical composition heals with the formation of a barrier film that protects the scar from environmental influences and ensures a certain amount of support to the scar. In one embodiment, the topical composition forms a thin film or crust when dry. This provides a certain amount of support to the scar and serves as a barrier from outside contamination, irritation from the sun, and cosmetics. Several embodiments of the topical composition described herein can advantageously be used without any tape or supporting structure because the synergic effect of the *Bulbine, Centella*, oleuropein and optionally silicone create a self-supporting barrier that does not require additional support. In several embodiments, a tape is not needed because non-scar conditions are treated, where support may not be needed.

In some embodiments, physical stimulation, such as by massage, needle (derma) rollers, is also incorporated as part of the regime for treating damaged skin. In one embodiment, a pre-treatment is provided prior to application of the topical compositions described herein. The pre-treatment includes, but is not limited to, exfoliation, physical stimulation, and energy-based stimulation (e.g., light, radiofrequency, ultrasound, microwave, etc.). The pre-treatment may be helpful to increase the absorption of the topical composition and/or work synergistically with the topical composition. The pre-treatment modalities described herein may also be used during and/or post-treatment.

Examples of Uses and Timing

In one embodiment, the topical compositions disclosed herein are used for controlling scar outcome and are applied at the time of wounding when the trigger for the sequence of healing begins or as soon thereafter as possible. In one embodiment, the topical composition is effective on scars that are several weeks, months or years old. In one embodiment, the topical composition prevents undesirable scarring. In one embodiment, the topical composition reduces one or more of the following characteristics of a scar by at least 25%, 50%, or 75%, as compared to a wound that is not treated with the composition: scar roughness, intensity of color, scar elevation and/or scar size. In some embodiments, the topical compositions may be helpful with keloid scarring, although the etiology of keloid scarring are generally very different from non-keloid scarring, and formulation adjustments may be needed.

In one embodiment, a method of treating a scar is provided, wherein the method comprises applying a topical composition disclosed herein to the scar at the time of provisional scar matrix formation to effect subsequent matrix dissolution and maturation. In one embodiment the treatment of the scar is commenced immediately following wound closure (e.g., at the time of surgery or injury), or within a day or two thereafter. In another embodiment, the wound is treated within 1-4 weeks of wound occurrence. In several embodiments, the invention comprises applying the topical composition to a scar that is weeks, months or years old to improve the appearance of the scar.

In some embodiments, the topical compositions provided herein are applied to scars or other undesirable marks on the skin, such as cellulite, stretch marks, wrinkles or age spots to improve the appearance of same. In other embodiments, the topical composition prevents the occurrence of cellulite, stretch marks, wrinkles, or age spots, and may be used on healthy or non-damaged skin. In some embodiments, because of the effects on collagen, the topical compositions help with skin laxity and are useful for skin tightening.

In several embodiments, the topical compositions provided herein are used to treat aged skin. In one embodiment, the treatment would be as follows: each morning a collagen booster such as phosphatidylserine (optionally combined with other ingredients, such as *Bulbine* for hydration) is applied to the skin together with an antioxidant and a sun protection cream. In the evening, the collagen booster (phosphatidylserine) is applied to the skin together with extracts of *Bulbine, Centella*, olive and optionally silicone and/or other ingredients. In one embodiment, a method of treating aged skin is provided, wherein the aged skin is characterized by a shortage of collagen and irregular collagen the fibrils of which are clumped or aggregated in nature. Young skin, on the other hand, is typically associated with uniform collagen fibers and good amounts of type 1 collagen. Several embodiments of the invention (i) stimulate of the formation of procollagen (e.g., because of the effect of the phosphatidylserine), (ii) stimulate of the formation of type 1 collagen (e.g., because of the *centella asiatica*), (iii) promote uniformly spaced collagen (e.g., due to the effect of the *Bulbine frutescens*), and/or (iv) mop up of free radicals that are associated with aging (e.g., due to the oleuropein and the *Centella asiatica*).

In one embodiment, the invention comprises a method of reducing free radicals and matrixmetalloproteinases MMP, e.g., type 1, wherein the method comprises: identifying damaged skin, applying (or instructing application of) a topical composition described herein to said damaged skin, thereby reducing free radicals.

In one embodiment, the invention comprises a method of increasing the formation of pro-collagen and/or type 1 collagen, wherein the method comprises: identifying damaged skin, applying (or instructing application of) a topical composition described herein to said damaged skin, thereby forming pro-collagen and/or type 1 collagen.

In one embodiment, the invention comprises a method of promoting uniformly spaced collagen, wherein the method comprises: identifying damaged skin, applying (or instructing application of) a topical composition described herein to said damaged skin, thereby promoting uniformly spaced collagen.

In one embodiment, the combination of *Centella asiatica, Bulbine frutescens* and oleuropein promote an increase in collagen and its sequential modulation to a well-structured form. In the context of collagen modulation, particularly when considering anti-aging intervention, the *Centella* extract, *Bulbine* extract, and oleuropein may be used in conjunction with phosphatidylserine, wherein the phosphatidylserine promotes the formation of procollagen, a collagen precursor and decreases the levels of MMP 1 which breaks down collagen and extracellular matrix components, characteristic of photodamage. This new collagen is then acted on by the combination of *Centella* extract, *Bulbine* extract, and oleuropein to induce maturation of the collagen. This embodiment of a topical composition acts synergistically to achieve important anti-aging benefits.

In one embodiment, the combination of *Centella* extract, *Bulbine* extract, oleuropein and phosphatidylserine may be used as an adjunct to anti-acne treatment. In this embodiment, the topical composition is used to minimize the eventual scarring resultant from the acne. In one embodiment, the topical composition is used once the acute pustular phase of the acne is ending and the inflammatory phase has started. The topical composition (e.g., in gel form) is applied to the individual acne lesions to promote healing, decrease inflammation and improve the final outcome in terms of scarring. There may well be beneficial effects in the early pustular phases of acne due to the antibacterial and anti-inflammatory effects of oleuropein and the healing effects of *Centella, Bulbine* and olive extracts, but, in one embodiment, the main indication in patients with acne would be for its use in diminishing scarring.

In several embodiments, the topical compositions described herein may be used to promote circulation and/or act as an anti-oxidant. Topical compositions according to several embodiments are useful in the treatment of dermal or subdermal infections. In one embodiment, varicose veins and/or spider veins are treated. In other embodiments, rosacea eczema, and/or psoriasis are treated. In several embodiments, use of the topical composition will reduce the scarring and pitting associated with chicken pox. In several embodiments, use of the topical composition is useful for insect bites and allergic reactions. In several embodiments, the compositions are used to treat burns. In several embodiments, such as burns, wounds or painful inflammation, the composition may additionally include or be administered with an analgesic (such as lidocaine, menthol, methyl salicylate, camphor, and/or capsaicin). In some embodiments, because pain-related neurotransmitters may generate fibrosis if they are continuously stimulated, the compositions disclosed herein comprise ingredients that reduce such neurotransmission. In one embodiment, sterols (e.g., plant sterols, β-sitosterols), flavonoids, alkaloids, etc. are provided to modulate neurotransmission to reduce pain and fibrosis. In one embodiment, the topical compositions disclosed herein are used before, during and/or following cosmetic surgery, or other surgery, to facilitate recovery and appearance. For example, the compositions disclosed herein may be used before, during or after chemical peels, laser resurfacing, energy-based aesthetic therapies (such as microwave, radiofrequency and ultrasound), filler injections, skin shavings, mole removals, biopsies and hair removal. Prior treatment with the topical composition may help prime the skin for later distress (e.g., due to a cosmetic procedure).

In several embodiments, the topical compositions described herein are formulated as moisturizers, body washes, soap, lotions, serums, eye creams, gels, sunscreens, bronzers, powders, nail care, hair care, foundation, blush, lip color, eye color and other cosmetics. In several embodiments, the topical compositions provided herein are useful for inclusion in shampoos, conditioners, and other hair treatments. In several embodiments, most or all of the ingredients are natural or organic. In many embodiments, the ingredients are non-comedogenic.

According to several embodiments, the present invention is primarily concerned with the treatment of human subjects, but the invention may also be carried out on non-human subjects, particularly mammalian subjects such as dogs, cats, livestock and horses for veterinary purposes. While subjects may be of any suitable age, the subjects are, in some embodiments, adult or geriatric subjects.

In several embodiments, the topical compositions described herein have sub-dermal effects. In one embodiment, the topical compositions modulate signaling mechanisms that interconnect the many layers of the dermis with the outer epidermal layer. In one embodiment, the topical compositions described herein modulate surface keratinocytes, which in turn orchestrate and initiate signaling events. In one embodiment, the topical compositions, with or without a scar tape, exhibit one or more of the following effects: SMAD7 inhibition of signaling to TGF-β, connexin 43 antagonism, connective tissue growth factor targeting, anti-SMAD2/3/4 complex, decreasing cadherin activation, and myofibroblast phenotype induction inhibition.

Several embodiments of the invention cause a decreased activation of keratinocyte signaling by mimicking stratum corneum function (hydration) resulting in decreased production of IL-1β (and probably other cytokines yet to be identified), increased production of antifibrotic tumor necrosis factor (TNF)-α clearing the extracellular matrix remnants and an increase in TGF-β3 via stimulation of the SMAD7 signaling mechanism. This may result in extracellular matrix remodeling with less inflammation, decreased collagen production, and balanced protease activity, collectively encouraging scar maturation.

Several embodiments of the invention prevent hypertrophic scar formation by, for example, simultaneous stimulation of SMAD7 expression and activation of proteasome degradation of SMAD3/4 signals. In one embodiment, plant-based phenols or other olive extracts play a role in stimulation. In one embodiment, oleuropein stimulates proteasomes to mop up extracellular fragments.

A short time (e.g., within an hour) after wounding, cyclooxygenase-2 (COX-2) enzyme may be activated to synthesize prostaglandins. Metabolites and enzymes of the arachidonic acid cascade, including the COX-2 enzyme and its enzymatic product prostaglandin E2 may mediate the inflammatory response. Thus, several embodiments of the invention inhibit this inflammatory pathway, thereby reducing scar formation and/or treating damaged skin.

Maturation of the inflammatory process may involve a progressive increase in TGF-β3. This growth factor isoform appears to be involved in cessation of matrix deposition. TGF-β3 reduces fibronectin and collagen deposition and is considered potently antifibrotic. Several embodiments of the invention modulate TGF-β3 levels. In one embodiment, *Centella* extracts increase TGF-β3 levels. In one embodiment, the topical compositions described herein contain other agents that modulate TGF-β3 activity, including recombinant TGF-β3.

Several embodiments of the invention, including but not limited to compositions comprising *Bulbine*, *Centella* and phenolic compounds (e.g., olive extracts), exhibit one or more of the following effects: increase SMAD7, increase TGF-β3, decrease TGF-β1, decrease COX-2, increase proteasome activation, and display potent antioxidant effects, and provide synergistic treatment of scars and other damaged skin.

The term "treat" as used herein shall be given its ordinary meaning and shall also include any type of treatment that imparts a benefit to a subject, e.g., delaying or retarding the progression of the condition. The condition, according to several embodiments, may be associated with aging, ultraviolet light exposure, wounds, surgery, infection, allergy, autoimmune effects, etc.

The term "pharmaceutically acceptable" as used herein shall be given its ordinary meaning and shall also include a compound or composition suitable for administration to a subject to achieve the treatments described herein, without unduly deleterious side effects in light of the severity of the disease and necessity of the treatment.

The term "extract" as used herein shall be given its ordinary meaning and shall also include one or more active agents or compounds (which may further include non-active components) obtained or isolated from a plant. Extracts may also include modified or synthetic versions of naturally-occurring compounds. Extracts may be, for example, mechanically or chemically purified or isolated from a plant source. The terms agents and ingredients may be used interchangeably.

The term "composition" as used herein shall be given its ordinary meaning and shall also include combinations or mixtures of one or more ingredients. A composition may include both active and inactive ingredients. Compositions may be oral, topical, or suitable for injection or other application. The terms compositions, medicaments and formulations may be used interchangeably.

Several embodiments of the invention will now be described by way of example with reference to the following non-limiting examples.

EXAMPLE 1

Sixty patients each having a scar following simple skin excisions formed part of this example. Thirty of the patients had their scars treated; thirty had their scars untreated (10 face, 10 limbs, 10 back in each group).

The treated patients were each treated as will be described with one embodiment of a scar gel of the invention. The scar gel comprised the ingredients and percentages as set out in Table 3.

TABLE 3

| Ingredient | Description or action in one embodiment |
| --- | --- |
| Aqua dest | Distilled water |
| Poloxamer | Gel Matrix |
| Glycerol-polyethylene glycol oxystearate | Surfactant. Helps in collecting oil droplets into aqueous gel matrix |
| Propylene glycol | Solvent |
| Dimethicone | Oil carrier; Silicone |
| Oleuropein (olive leaf extract) | Antiseptic properties (anti-fungal; anti bacterial and anti inflammatory |
| Triterpenic fraction of *Centella asiatica* | Reducer of Scar tissue This converts collagen III to collagen I |
| Phenoxyethanol | Preservative against fungi |
| Methylhydroxy-benzoate | Preservative against germs |
| Lactic acid | To bring acidity of the product to near skin pH which is lower than 5.5 |
| *Bulbine Frutescens* | For re-arranging collagen fibrils. |
| Microporous tape | Optional Support |

In one embodiment, the triterpenic fraction of *Centella asiatica* comprises 0.5% m/m of the medicament; the *Bulbine Frutescens* comprises 10.0% m/m of the medicament, and the oleuropein comprises 0.18% to 0.3 mass/volume of the medicament.

Patients were randomized to receive either routine post-operative care with tape alone (bilateral cosmetic cases) (the untreated patients) or combined tape with topical scar gel or no treatment (routine for small skin excisions) (the treated patients). Where one side was treated, the side selected for treatment was also randomized (at the end of surgery, the nursing staff drew lots to choose the right or left side for treatment). All scars were assessed and photographed at follow-up at 1, 2, and 6 months following surgery.

In contrast to known management programs, scar management was initiated in the treated patients immediately following surgery.

For small local excisions of skin tumors, the wounds were left without a dressing on the face and gel was applied directly to the site and continued twice daily by the patient as long as desired and normally for the full six month period.

In an effort to combine all recent recommendations for scar assessment, elements of different scales were incorporated into the assessment parameters. Thus, elements of the Vancouver Scar Scale were incorporated into the scale of morphologic features. Patient and observer assessment charts were also included in the assessments as previously recommended.

The data were revised into a format compatible with the statistical program using SAS v9. Differences between treated and untreated patients were determined using the Kruskal/Wallis test with $p<0.05$ considered significant.

In the patients there were no significant differences apparent one month after the operation, the scars were significantly improved after two months in the treated versus the untreated group. Over the six months the morphologic grading scores improved only in treated but not untreated patients.

Scar thickness and regularity of the treated scars were rated as being significantly better than untreated scars, with scar stiffness reaching borderline significance.

Observers rated scar vascularization, pigmentation, thickness, relief, and pliability of the scar. All these parameters were significantly improved ($p<0.005$) in treated patients compared with the parameters of untreated patients.

Observers noted scar hypopigmentation, hyperpigmentation, and mixed (hypo/hyperpigmentation) scars in 16 of the treated patients (89%). This compared favorably ($p=0.04$) with the untreated patients in whom $14/23$ (61%), $4/23$, and $5/23$ had hypo-, hyper-, and mixed pigmentation (hypo/hyperpigmentation) scars respectively.

EXAMPLE II

In another non-limiting example, twenty patients each patient with two excisions formed part of this study. Of the two excisions of each patient, one was treated and one untreated (10 back, 5 face, 5 limbs).

On the back and limbs the site was covered with microporous tape. Scar gel was applied immediately following surgery on to the surface of the tape, saturating it and producing an occlusive type of dressing. Patients were instructed to apply scar gel to the surface of the tape twice a day morning and night.

The scar assessment was as indicated above. In patients with two excisions where one was treated and the other not (Group 1) the differences in scar morphology became significantly apparent at 6 months. As with Example 1, the treated but not the untreated scars showed significant improvement over the 6 months.

Observers rated scar vascularization, pigmentation, thickness, relief, and pliability of the scar. Except for the vascularization rating, all other parameters were significantly improved.

EXAMPLE III

Ten patients undergoing skin surgery were treated with the scar gel as set out in Table 3. The ten patients had 20 scars following bilateral breast surgery, one side treated with tape alone, one side treated with tape and gel (5 breast augmentations, 5 breast reductions).

In patients to whom the gel was applied, the scar gel was applied liberally to the area prior to application of the dressing. The gel was not massaged in but was left on the surface to ensure a reasonable amount of gel on the scar surface while the dressing was left undisturbed for seven to ten days.

In cases where the dressing was changed the following day (breast reduction procedures), scar gel was reapplied to the selected side. Following the dressing change after seven to ten days, patients continued with the program for three to six months until the scar was considered mature (nonsymptomatic, white). The scar assessment was as indicated above.

Similar results were found for this group of breast augmentation and reduction patients. Treated scars showed significant morphologic improvement after two months with borderline significance at 1 and 6 months compared to the untreated scars (i.e. the scars treated by tape alone).

Only treated scars showed significant improvement in itchiness, with scar stiffness, thickness, and regularity approaching significance. Observers rated scar vascularization, pigmentation, thickness, relief, and pliability of the scar. Vascularization and pigmentation were improved in treated scars with scar thickness, relief, and pliability reaching borderline significance.

Early scar control starting at the time of wounding is new in the improvement of scar outcome. Thus although the application of the scar gel can be commenced from seven to fourteen days after surgery preferably the scar gel is applied at the time of initial dressing at the end of the surgical procedure or the following day after surgery and as an immediate and continued application to the wound for small local excisions of skin lesions was applied in all the Examples. Efficacy was particularly evident in the patients mentioned in Example III where those treated immediately with tape and scar gel had better outcomes in all parameters measured.

EXAMPLE IV

Thirty patients with varying cosmetic procedures with 50 scars all treated and compared with historical outcomes for hypertrophic scarring (10 breast augmentations, 10 breast reductions, 10 abdominoplasties). The scars were treated immediately after surgery with the scar gel mentioned in Table 3.

The scar assessment was as indicated above. The results showed that these patients who underwent a variety of procedures and showed improvement in scar morphology over the 6 months of follow-up. Overall morphology improved in all the groups.

Observers rated scar vascularization, pigmentation, thickness, relief, and pliability of the scar. All these parameters were significantly improved ($p<0.005$) in treated patients compared with the parameters of untreated patients. Observers noted scar hyperpigmentation were similar in the treated patients in Example I.

It will be seen therefore that in the important areas of scar assessment, the patients treated in all examples showed statistically significant improvement in all parameters. Morphologic features together with stiffness, thickness, and irregularity in POSA and thickness and relief in OSA are probably the most important parameters for analysing scar hypertrophy.

A number of patients had undergone previous surgery. The first scars (i.e. from the previous surgery) were compared with those produced by the new surgical procedure where the scar program was used. In two of these cases previous infra-mammary scars were excised in patients who had undergone reduction surgery elsewhere. The new infra-mammary scars demonstrated superior scar outcomes to those of the previous mid-line and periareolar scars. Morphologic assessment of scars at two months (not one month) were usually (although not always) reasonable predictors of long-term scar outcome. Predictors of poor outcome of long-term scar results appeared to be that of early signs of scar thickening or hypertrophy (Grade 3 morphologic scale).

In the examples set forth above, support by microporous tape may not be needed, for example in cases where the wound is supported by subcuticular sutures. In one embodiment, tape is also not needed for smaller excisions or skin lesions, where tension on the skin is expected to be much less in these cases. In one embodiment, the invention results in a multimodal treatment that results in hydration, controlled inflammation, and collagen maturation in which the ingredients act synergistically to convert the microporous tape to an occlusive interactive. In several embodiments, the combination of ingredients (e.g., *Bulbine, Centella* and olive extracts, etc.) shows marked improvement over ingredients that only provide hydration.

One skilled in the art will readily appreciate that embodiments of the present invention are well adapted to carry out the objects and obtain the ends and advantages mentioned, as well as those inherent therein. The present examples along with the methods, procedures, treatments, molecules, and specific ingredients described herein are presently representative of several embodiments, and are not intended as limitations on the scope of the invention. Changes therein and other uses which are encompassed within the spirit of the invention may be defined by the scope of the claims.

What is claimed is:

1. A method for treating scarred skin, said method comprising:
    applying at least one extract of *Bulbine frutescens* to the scarred skin, in an amount from about 1.25 mg to 25 mg;
    applying at least one extract of *Centella asiatica* to the scarred skin, in an amount from about 0.5 mg to 25 mg.
    applying oleuropein to the scarred skin, in an amount from about 0.5 mg to 2.5 mg; and
    applying dimethicone, poloxamer, and propylene glycol to the scarred skin;
    wherein said Bulbine frutescens, *Centella asiatica*, oleuropein, dimethicone, poloxamer, and propylene glycol are applied daily and simultaneously.

2. The method of claim 1, further comprising applying at least one of the following:
    water;
    at least one preservative;
    at least one gelling agent;
    at least one solvent;
    at least one pH balancing agent; and
    at least one surfactant.

3. The method of claim 1, further comprising providing a dual-chambered device that separates the *Bulbine, Centella*, oleuropein and silicone from one or more additional ingredients.

* * * * *